US00PP15437P3

(12) United States Plant Patent

Pecota et al.

(10) Patent No.: US PP15,437 P3
(45) Date of Patent: Dec. 21, 2004

(54) ORNAMENTAL SWEETPOTATO PLANT NAMED 'SWEET CAROLINE BRONZE'

(50) Latin Name: *Ipomoea batatas*
Varietal Denomination: Sweet Caroline Bronze

(75) Inventors: Kenneth Pecota, Raleigh, NC (US); G. Craig Yencho, Washington, NC (US); Cynthia Pierce, Clayton, NC (US)

(73) Assignee: North Carolina State University, Raleigh, NC (US)

( * ) Notice: Subject to any disclaimer, the term of this patent is extended or adjusted under 35 U.S.C. 154(b) by 27 days.

(21) Appl. No.: 10/114,489

(22) Filed: Apr. 2, 2002

(65) Prior Publication Data

US 2003/0188360 P1 Oct. 2, 2003

(51) Int. Cl.[7] ..... A01H 5/00
(52) U.S. Cl. ..... Plt./258
(58) Field of Search ..... Plt./258

(56) References Cited

PUBLICATIONS

Armitage, Allan M. and James M. Garner, "*Ipomoea batatas* 'Margarita,'" *HortScience*: 36(1) 178 (Feb. 2001).
Armitage, Allan M., "Sweet Potato," *Greenhouse Grower*: 103–104 (Mar. 1999).
Baggett, "Sweet potato vines are morning glory cousins," *Fine Gardening*: 84 (Apr. 2002).
Bodger Seeds, Ltd., "2001 Pack Trails" invitation, Apr. 3–12, 2001.
Bodger Seeds, Ltd., "2001 Pack Trials" brochure, p. 13, Apr. 3–12, 2001.
Bodger Botanicals catalog, Sep./Oct.: p. 6 (2001).
North Carolina State University, "New Sweet Potatoes Add Ornamental Flavor, " *Extension's Successful Garden*: p. 1 (Mar. 2002).
Online catalog selling Ipomea cultivars: www.glasshouse-workscom/trop–ij.html p. 4, date of access: Aug. 15, 2002.
Online catalog selling Ipomea cultivars: www.sunnyfield.com/varietylists/companionplants.html p. 5, date of access: Aug. 15, 2002.
Online catalog selling Ipomea cultivars: www.papgenos.com/plantdb/plants.asp?catid=15 pp. 1–4, date of access: Aug. 15, 2002.
"Ornamental Sweet Potatoes," www.Inla.org/ornpotato.html pp. 1–2, updated Jun. 4, 2000, date of access: Aug. 15, 2002.
"Bodger Seeds/Botanicals," *Greenhouse Grower* (Jun. 2001).

*Primary Examiner*—Kent Bell
(74) *Attorney, Agent, or Firm*—Myers Bigel Sibley & Sajovec, P.A.

(57) ABSTRACT

A new and distinct ornamental cultivar of *Ipomoea batatas* called 'Sweet Caroline Bronze' is described as having a compact, mounded appearance with dense foliage and with a leaf shape typical of morning glory. The plant is distinguished from current cultivars known to the inventors by its striking color combination; mature leaves have a bronze to purple-bronze color with purple veins and stems which contrast sharply with the new shoots, which are chartreuse in color. Furthermore, this plant has good vigor and flowers under short day conditions. *Ipomoea batatas* 'Sweet Caroline Bronze' is suitable for use in landscaping and containerized gardens.

7 Drawing Sheets

Latin name of the genus and species: The Latin name of the novel, ornamental plant variety disclosed herein is *Ipomoea batatas* (L.) Lam.

Variety Denomination:

The inventive cultivar of *Ipomoea batatas* disclosed herein has been given the variety denomination 'Sweet Caroline Bronze'.

BACKGROUND OF THE INVENTION

*Ipomoea batatas* species are members of the morning glory family Convolvulaceae. *Ipomoea batatas,* commonly referred to as the white or yellow sweetpotato and the orange yarn, are typically fast growing vines with palmately-lobed leaves. These ornamental species produce storage roots identical in appearance to the common sweet potato, but not as palatable. Late in the growing season, tubular flowers appear which are similar to morning glories, but plantings are dominated by the appearance of the foliage. The plants are highly desirable due to their ability to grow under varied stress conditions, cover a large space, and last the entire growing season. Moreover, these plants have few insect or disease problems.

Existing varieties of *Ipomoea batatas* are popular for landscaping applications. There are currently six common types of ornamental sweetpotatoes that are being cultivated primarily for annual, summer vines. These six cultivars are: 'Blackie' (unpatented), having dark purple-black foliage, lavender flowers, and edible storage roots; 'Terrace Lime' (unpatented) and 'Margarita' (unpatented; also known as 'Sulfur'), which have large brilliant chartreuse leaves and lavender blooms; 'Black Heart' (unpatented; also known as 'Ace of Spades'), having heart-shaped leaves with burgundy purple color; 'Tricolor' (unpatented; also known as 'Pink Frost'), is a variegated plant which has pale green, white, and pink-margined leaves; and 'Lady Fingers' (unpatented), which has medium green, dainty leaves divided into long, thin, fingerlike lobes which are complemented by burgundy stems and veins.

*Ipomoea batatas* 'Margarita' has recently been released in the United States, and has become widely used as a landscape annual. It is not suitable for mixed containers, as this variety exhibits a very vigorous growth and tends to out-compete other species. Another popular variety is 'Blackie', a vigorous purple-leaved clone which is also unsuited to containerized gardens. See Armitage. A. M. and J. M. Garner, 2001. *Ipomoea batatas* 'Margarita'. HortScience 36:178.

Therefore, to meet the current horticultural demand, it is desirable to produce new, more robust cultivars of ornamental sweetpotato with attractive foliage colors, leaf shapes, and plant architectures. In addition, it would be advantageous to develop cultivars or ornamental sweetpotato exhibiting a more compact growth, and which do not out-compete other species in mixed containers.

The present invention comprises a new and distinct variety of *Ipomoea batatas,* which has been named 'Sweet Caroline Bronze'. The variety is suitable for use as a landscape or containerized plant.

Lineage. The *Ipomoea batatas* 'Sweet Caroline Bronze' cultivar originated from a conventional cross between *Ipomoea batatas* cultivars 'Sulfur' (the female parent; not patented, from which 'Margarita' was propagated) and NCSXBR5-18ORN (the male parent; not patented) conducted in the Winter of 1999–2000 at the Horticultural Greenhouses located at North Carolina State University, Raleigh, N.C. Seeds from this cross were planted in the Horticultural Greenhouses in Spring 2000. The single, individual plant now known as *Ipomoea batatas* 'Sweet Caroline Bronze' was selected in July 2000 because of its combination of exceptional features, and has been propagated asexually since that time.

Asexual Reproduction. Since its selection, *Ipomoea batatas* 'Sweet Caroline Bronze' has been asexually reproduced at the Horticultural Greenhouses located at North Carolina State University, Raleigh, N.C. predominantly by vegetative propagation of vine cuttings. Asexual propagation of the new cultivar by cuttings at the location previously stated has shown that the unique features of this new Ornamental Sweetpotato are stable and the plant reproduces true to type in successive generations of asexual propagation.

SUMMARY OF THE INVENTION

The present *Ipomoea batatas* 'Sweet Caroline Bronze' ornamental plant has a very distinct coloration; new shoots are chartreuse green in color, while mature leaves have a bronze to purple-bronze color with purple veins and stems. The leaves are moderately lobed with three to five lobes. 'Sweet Caroline Bronze' has a compact, mounded shape with dense foliage. Furthermore, this plant has good vigor. Cultivar 'Sweet Caroline Bronze' will flower under short day conditions.

DETAILED BOTANICAL DESCRIPTION

The following is a detailed description of the botanical characteristics of a new and distinct cultivar of *Ipomoea batatas* plant known by the cultivar name *Ipomoea batatas* 'Sweet Caroline Bronze'. All colors cited herein refer to *The Royal Horticultural Society Colour Chart* (The Royal Horticultural Society, London, 1995 edition) designations except where general terms of ordinary dictionary significance are used. When dimensions, sizes, colors, and other characteristics are given, it is to be understood that such characteristics are approximations or averages set forth as accurately as practicable.

The descriptions reported herein are from 12-week-old plants grown individual in six-inch azalea pots. The plants were grown in Lompoc, Calif., under commercial practice in a polycarbonate-covered greenhouse during the 2001–2002 winter with day and night temperatures ranging between 18.3–26.7° C. and 15.6–18.3° C., respectively, and light levels of about 4,000–8,000 foot-candles. *Ipomoea batatas* 'Sweet Caroline Bronze' has not been observed under all possible environmental conditions; therefore, the phenotype may vary with variations in the environmental such as season, temperature, light intensity, day length, cultural conditions, and the like.

Growth Conditions. *Ipomoea batatas* 'Sweet Caroline Bronze' has good vigor, a moderate growth rate, and is very adaptable to container culture. In locales with mild winter conditions, *Ipomoea batatas* 'Sweet Caroline Bronze' will grow perennially; otherwise it is an annual plant that is killed by frost. In the greenhouse setting described above, after twelve weeks of growth, plants of this cultivar produce compact, round-mounded, herbaceous plants averaging 12 cm in height and 30 cm in length. Similar to cultivated sweetpotatoes, wind or rain rarely causes much damage to 'Sweet Caroline Bronze', but if damage does occur, the plant drops the damaged leaves and grows new shoots at nodes where the leaves were lost. Under low light levels in a greenhouse, 'Sweet Caroline Bronze' can develop intumescence, which will remain on the affected foliage, but will be outgrown with new foliage.

Figure 1:
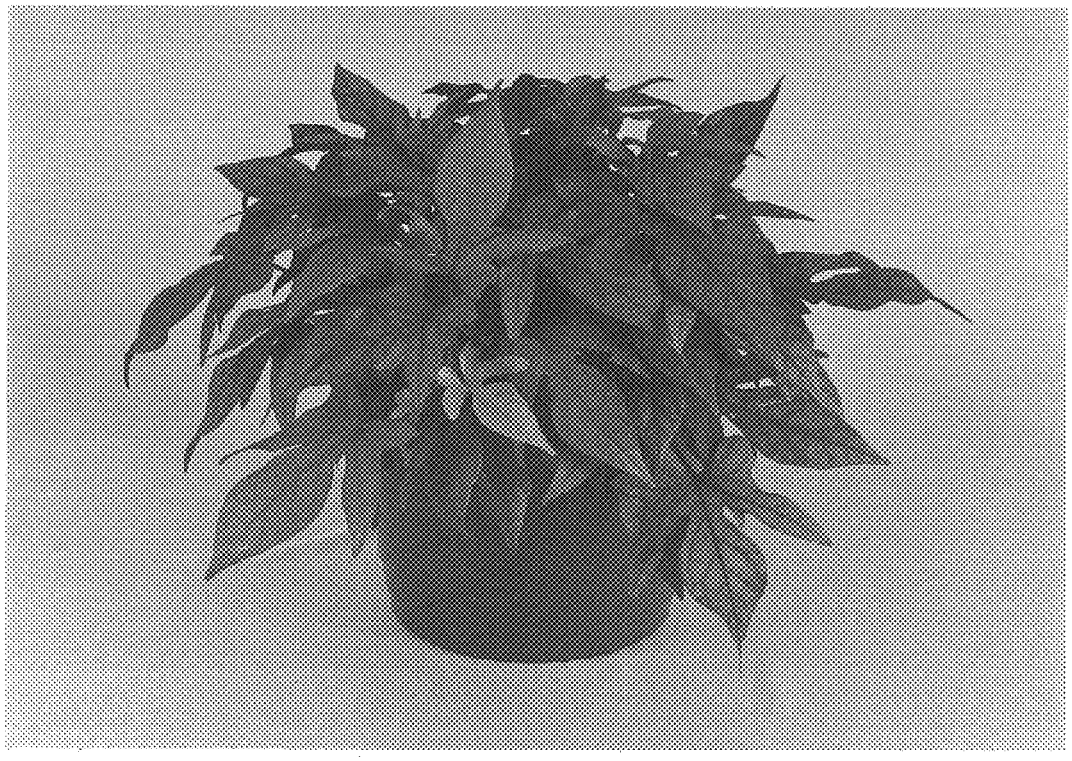
FIG. 1 is a color photograph of a typical plant of *Ipomoea batatas* 'Sweet Caroline Bronze' grown in a container under commercial greenhouse conditions.
Figure 3:
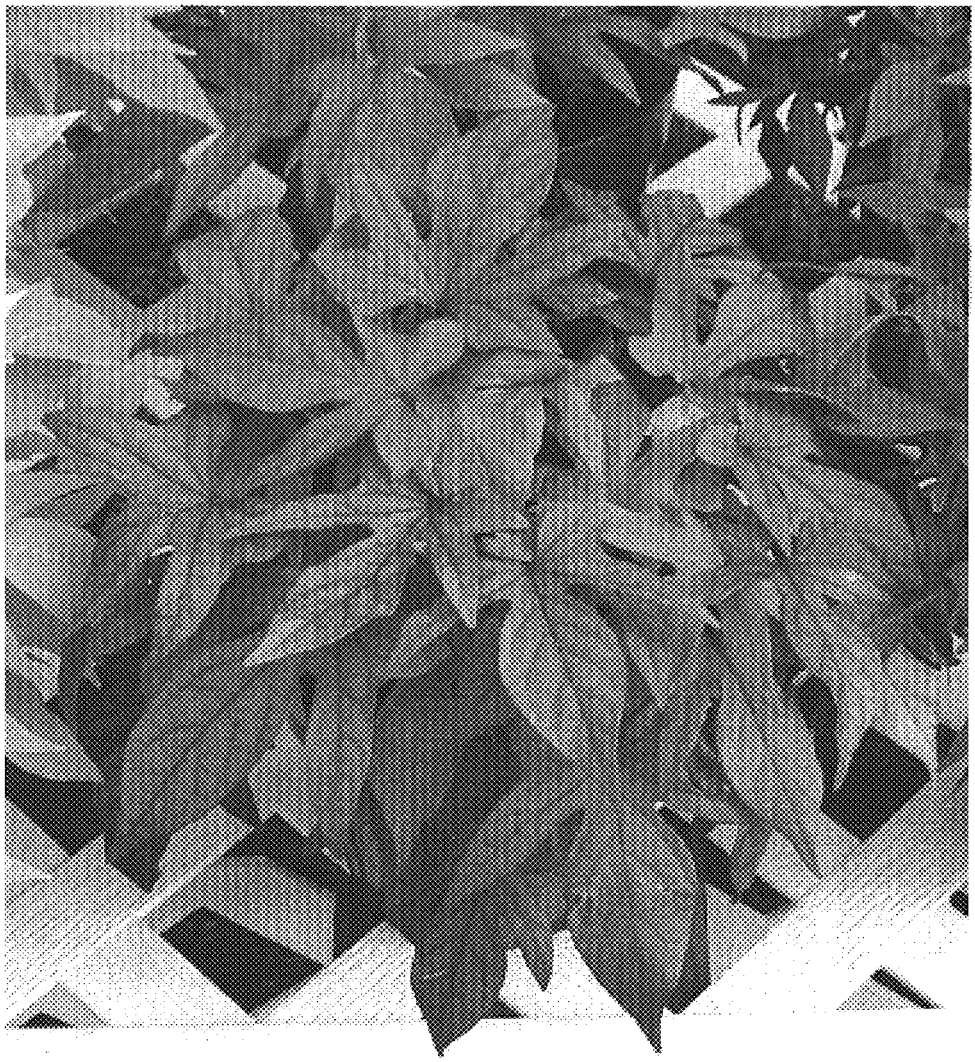
FIG. 3 shows a top view of a typical plant of the *Ipomoea batatas* 'Sweet Caroline Bronze' grown in a container under commercial greenhouse conditions.

Above-Ground Structure and Coloration. FIGS. 1 and 3 shows the shape and distinctive coloration of typical *plants* of *Ipomoea batatas* 'Sweet Caroline Bronze'. Overall, this cultivar is a compact, mounded, and outwardly-spreading, herbaceous plant with a dense canopy that has an average height of 12.0 cm and an average area of spread of 30×30 cm.

Branching Habitat. Excellent branching with ~12 lateral branches coming off the stem. Very dense foliage with no pinching required to stimulate branching.

Stem (Color: 186A). Round with white hairs and good strength. Length: ~7.0 cm. Diameter: ~0.4 cm. Internodes are short with an average length of ~0.7 cm. Outward aspect with soft zigzag at the nodes.

Vegetative Lateral Branches (Color: 186A). Same as stems for most characteristics. Length: ~7.0 cm. Diameter: ~0.4 cm. Internodes are short with an average length of ~0.7 cm.

Petiole (Color: 59A). Length: ~11.0 cm. Diameter: ~0.25 cm.

Foliage. Leaves are alternate and simple. Further, the leaves are palmate with three, deep-parted sinuses. Quantity: Densely foliated, with ~10 leaves per lateral branch. Mature leaf length: ~11.0 cm with broad variation. Mature leaf with: ~12.0 cm. Leaf margin is entire. Lobe length: 5.0 cm. Mid-vein lobe with: ~4.5 cm. Leaf apex: Acute. Leaf base: Acute. Leaf has a smooth texture and matte finish. Venation is palmate at the base with pinnate to arcuate veins in the mid-vein lobe. Color: Table 1.

TABLE 1

| Leaf Structure | Upper Surface | Lower Surface |
|---|---|---|
| Young Leaf | Slightly Greener than 153A* | 146C |
| Mature Leaf | More Gray-Red than 199A*# | More Gray than 183D* |
| Vein | 59B | 61A |

*The color does not match any color provided in the Royal Horticultural Society Colour Chart.
#Can best be described as a bronzed look achieved by a yellow-green base color overlaid with anthocyanins.

Figure 4:
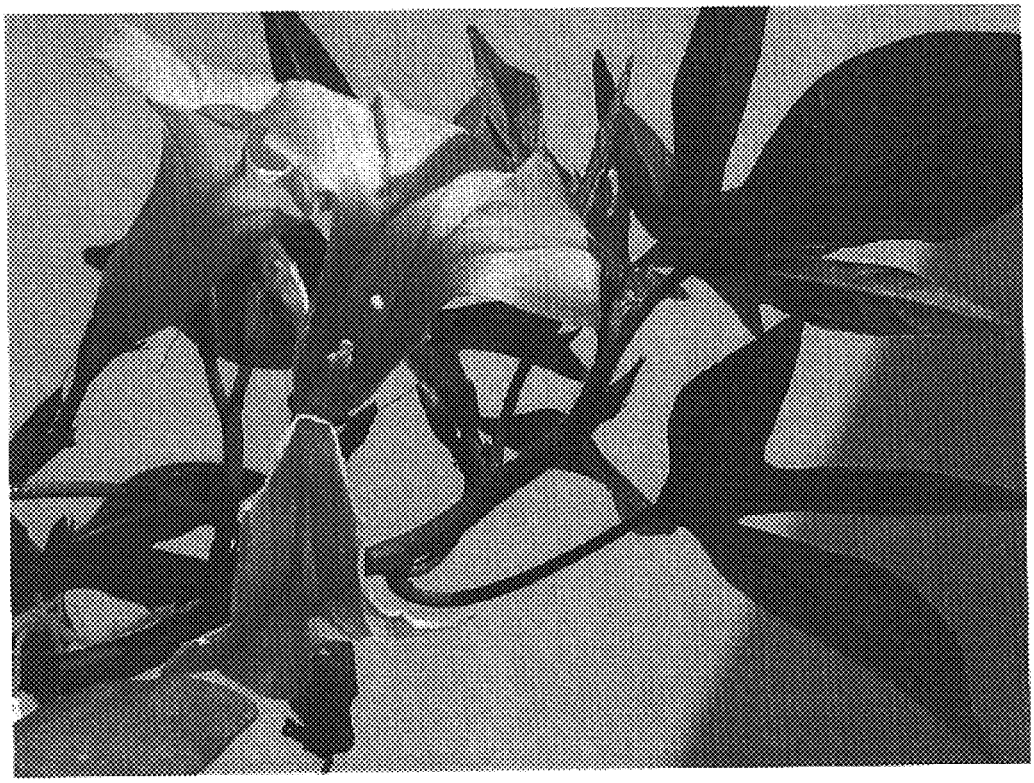
FIG. 4 shows a side view of a flower produced by 'Sweet Caroline Bronze' with a petal peeled back to reveal interior structures.
Figure 5:
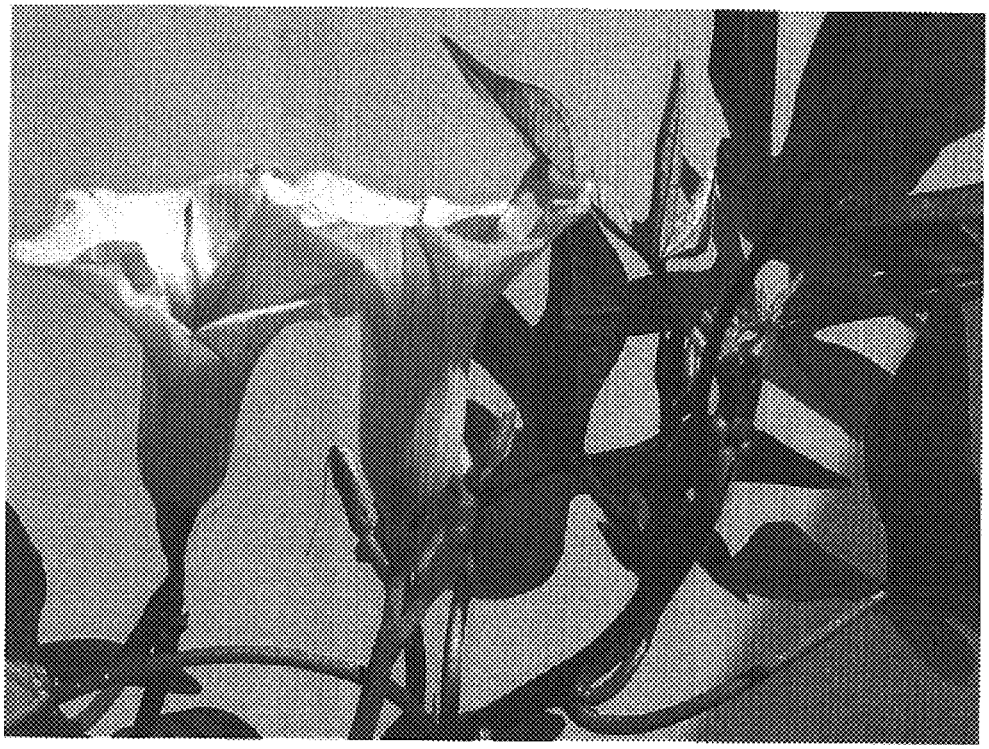
FIG. 5 shows a side view of intact flowers produced by 'Sweet Caroline Bronze'.
Figure 6:
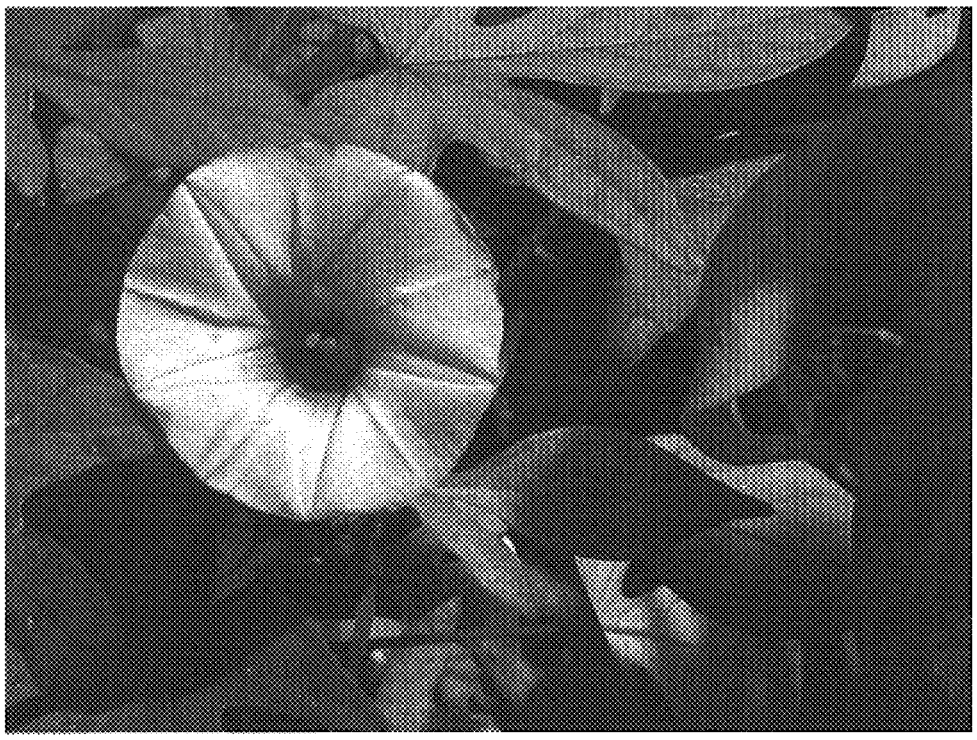
FIG. 6 is a top view of an intact flower produced by 'Sweet Caroline Bronze'.

Flowers. 'Sweet Caroline Bronze' flowers sporadically throughout the season in response to a variety of stressful conditions (e.g., drought, nutrient stress, cloudy weather). Flowering is enhanced by shorter day lengths, but the precise photoperiod for flower induction is currently unknown. FIGS. 4, 5 and 6 show views of typical flowers of the variety. The inflorescence is generally a cyme in which the peduncle is divided into two axillary peduncles. Each peduncle is further divided into two after the flower is produced. Peduncles (Color: 187C) are purple, averaging around 33 mm long from mature leaf axils with an average diameter of 2.4 mm. Usually buds of the first, second and third order are developed, but sometimes single flowers are produced. Buds (Color: 186B to 186C) are purple colored, ovate, and around 25 mm in length and 5 mm in diameter 24 hours before opening. The corolla is composed of five fused petals that form a funnel with a round limb. Corolla width: ~4.5 cm, corolla length: ~4.4 cm. The corolla is not fragrant. The limb and outer throat are lavender and the inner throat purple. Inner limb color: 77D, Outer limb color: 77D, Inner throat color: 77A, Outer throat color: 77D. There are five sepals, with an average length of 10.4 mm and width of 3.4 mm. The sepals are ovate with an acute apex and purple in color. Outer sepal color: 186A, Inner sepal color: 186B. Each flower has on pistil, with a cream colored style (Color: 155A) with a length averaging 24 mm. The stigma is cream colored (Color: 156D) and averages about 1.6 mm wide and 2.0 mm long and has two segments. The stigma is exerted relative to the stamens. The ovary is yellow (Color: 160B) and superior with two locules that contain one or two ovules. At the base of the ovary there are orange basal glands (Color: 167A to 167B) containing nectar. There are five cream colored anthers (Color: 158B) that are approximately 3 mm long. Pollen (Color: 158B) is abundant. True seed are relatively easy to obtain in compatible crosses. There is some variation in flower size and color, depending on the environmental conditions. Descriptions are based on: CIP, AVRDC, IBPGR. 1991. Descriptors for Sweet Potato. Huaman, Z., editor. International Board for Plant Genetic Resources, Rome, Italy.

Figure 2:
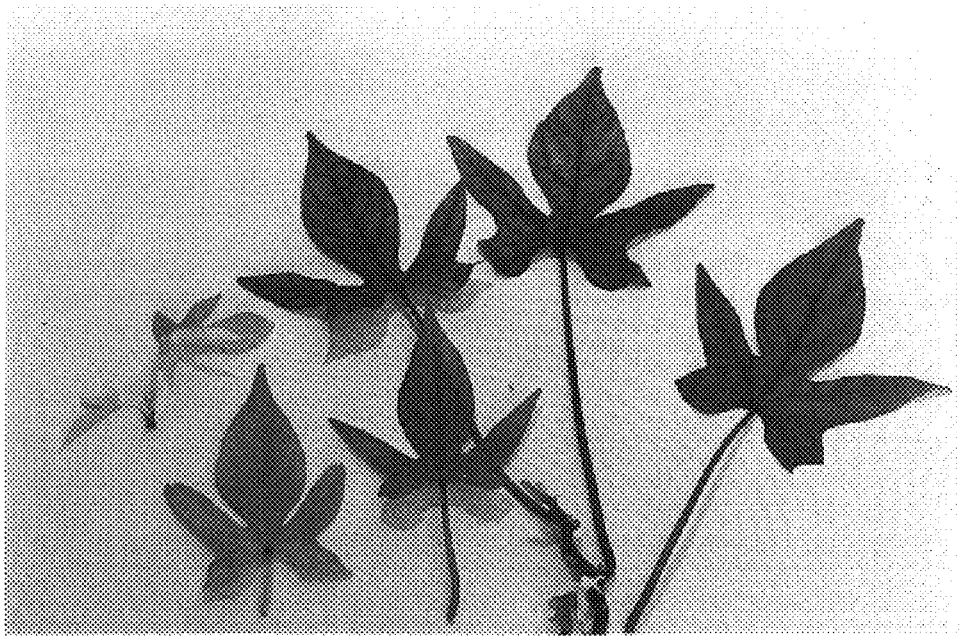
FIG. 2 shows the variety of leaves produced by *Ipomoea batatas* 'Sweet Caroline Bronze' and the lower surface of the leaf (lower right leaf).

Color Variation. *Ipomoea batatas* 'Sweet Caroline Bronze' has a very striking color combination. The new shoots are chartreuse-green (FIG. 2, lower leaf leaves) and as the leaves mature, they develop the characteristics bronze color with purple veins and stems (FIG. 2, lower, center leaf). As the leaf ages, it develops a more purple-bronze color (FIG. 2, upper, center leaves) and the back of the leaf is purple (FIG. 2, lower right leaf). This purple-bronze color develops with exposure to sunlight and is most predominant in the upper canopy. Leaves inside the canopy are not as dark.

Leaf color of *Ipomoea batatas* 'Sweet Caroline Bronze' can range from bronze to red depending on the environment. Lower temperatures favor anthocyanin pigment development and plants tend to be more reddish. Higher temperatures reduce red pigmentation and leaf color is more bronze.

Figure 7:
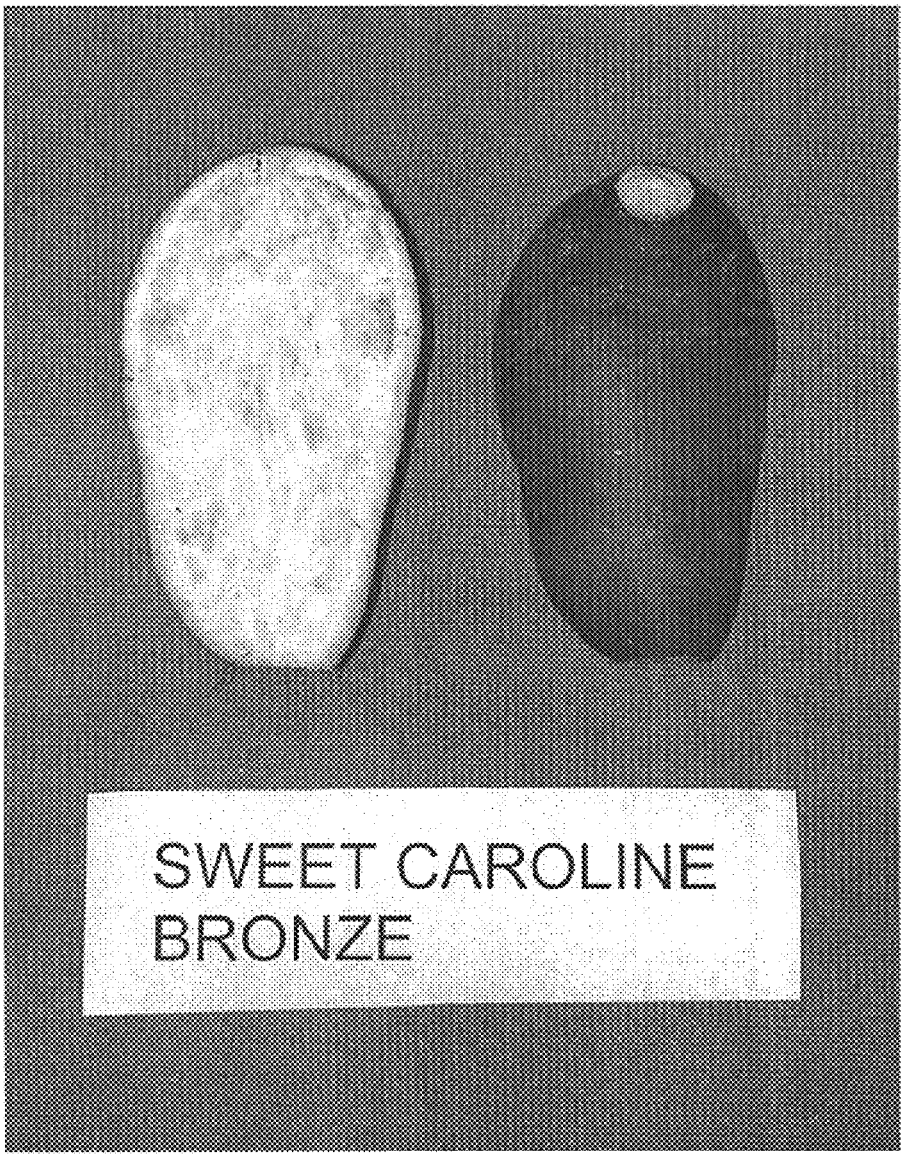
FIG. 7 shows the flesh and skin of a storage root.

Storage Roots. As shown in FIG. 7, the storage roots have a purple skin (Color between 186A and 186B) and cream-colored flesh (Color: 158B) with traces of purple (Color 186B). Shapes are highly irregular and vary considerably in length and diameter depending on growing conditions. A minimum of 130 days are needed to produce storage roots that meet the size criteria for United States Department of Agriculture (USDA) U.S. No. 1 grade (5.1–8.9 cm in diameter and 7.6 to 22.9 cm in length), but very few of these storage roots would meet the shape criteria for U.S. No. 1 grade. Under conditions in which the plant grows perennially, the storage roots will continue to grow as long as they are healthy and the weather remains warm.

Comparison with Other *Ipomoea batatas* Cultivars. Compared with the six most common cultivars of ornamental sweetpotato, *Ipomoea batatas* 'Sweet Caroline Bronze' is very distinct. The coloration of the foliage is unique, and there are no suitable comparators among existing cultivars of *Ipomoea batatas* known to the invertors.

Likewise, in a comparison with the parental strains, 'Sweet Caroline Bronze' is quite distinct from each parent (Table 2).

TABLE 2

| | 'Sweet Caroline | Female Parent | Male Parent |
|---|---|---|---|
| Characteristic | Bronze' | 'Sulfur' | NCSXBR5-18ORN |
| Foliage Color | Bronze to Red | Yellow | Purple |
| Leaf shape | Moderately to Deeply Lobed | Slightly Lobed | Moderately Lobed |
| Storage Root Skin Color | Purple (between 186A and 186B) | Purple (between 78A and 78B) | Cream (158B) |
| Storage Root Flesh Color | Cream (158B) Purple (186B) | Cream (158B) | Cream (158A) |
| Plant Habit | Moderately to Well Branched | Moderately branched | Few Branches |

Disease or Pest Resistance. 'Sweet Caroline Bronze' is susceptible to Sweetpotato Feathery Mottle Virus and damage by Japanese beetles.

Herbarium voucher. A voucher of 'Sweet Caroline Bronze' will be deposited into the Herbarium of North Carolina State University (NCSU) in Raleigh, N.C. upon patenting.

What is claimed is:

1. A new and distinct cultivar of *Ipomoea batatas* plant named 'Sweet Caroline Bronze', substantially as illustrated and described herein.

* * * * *